United States Patent

Hara et al.

[11] Patent Number: 5,461,238
[45] Date of Patent: Oct. 24, 1995

[54] RADIATION IMAGE READ-OUT APPARATUS

[75] Inventors: Shoji Hara; Satoshi Arakawa, both of Kanagawa, Japan

[73] Assignee: Fuji Photo Film Co., Ltd., Kanagawa, Japan

[21] Appl. No.: 325,474

[22] Filed: Oct. 19, 1994

[30] Foreign Application Priority Data

Oct. 25, 1993 [JP] Japan ................... 5-266208

[51] Int. Cl.$^6$ ................... G01N 23/04
[52] U.S. Cl. ............ 250/587; 250/586; 250/201.1
[58] Field of Search .................... 250/587, 586, 250/584, 484.4, 201.1, 205

[56] References Cited

U.S. PATENT DOCUMENTS 5,081,356  1/1992  Korikawa .................... 250/586
5,264,690  11/1993  Hill .................... 250/201.1

FOREIGN PATENT DOCUMENTS 1274128  11/1989  Japan .................... 250/586

*Primary Examiner*—Davis L. Willis
*Assistant Examiner*—Richard Hanig
*Attorney, Agent, or Firm*—Sughrue, Mion, Zinn, Macpeak & Seas

[57] ABSTRACT

In a radiation image read-out apparatus, a stimulable phosphor sheet, on which a radiation image has been stored, is exposed to stimulating rays, which cause the stimulable phosphor sheet to emit light in proportion to the amount of energy stored thereon during its exposure to radiation. The emitted light is detected and photoelectrically converted by a photodetector, and an image signal representing the radiation image is thereby generated by the photodetector. Information corresponding to the amount of energy stored on the stimulable phosphor sheet during its exposure to radiation is inputted from a stored energy amount input device. A light amount adjuster is located in an optical path of the emitted light impinging upon the photodetector in order to adjust the amount of the emitted light impinging upon the photodetector in accordance with the amount of energy stored on the stimulable phosphor sheet, which energy amount is represented by the information having been inputted with the stored energy amount input device.

12 Claims, 3 Drawing Sheets

RADIATION IMAGE READ-OUT APPARATUS

BACKGROUND OF THE INVENTION

1. Field of the Invention

This invention relates to a radiation image read-out apparatus. This invention particularly relates to a radiation image read-out apparatus, wherein a stimulable phosphor sheet, on which a radiation image has been stored, is exposed to stimulating rays, which cause the stimulable phosphor sheet to emit light in proportion to the amount of energy stored thereon during its exposure to radiation, and the emitted light is detected and photoelectrically converted by a photodetector.

2. Description of the Prior Art

Techniques for reading out a recorded radiation image in order to obtain an image signal, carrying out appropriate image processing on the image signal, and then reproducing a visible image by use of the processed image signal have heretofore been known in various fields. For example, an X-ray image is recorded on an X-ray film having a small gamma value chosen according to the type of image processing to be carried out, the X-ray image is read out from the X-ray film and converted into an electric signal (i.e., an image signal), and the image signal is processed and then used for reproducing the X-ray image as a visible image on a photocopy, or the like. In this manner, a visible image having good image quality with high contrast, high sharpness, high graininess, or the like, can be reproduced.

Further, it has been proposed to use stimulable phosphors in radiation image recording and reproducing systems. Specifically, a radiation image of an object, such as a human body, is recorded on a sheet provided with a layer of the stimulable phosphor (hereinafter referred to as a stimulable phosphor sheet). The stimulable phosphor sheet, on which the radiation image has been stored, is then scanned with stimulating rays, such as a laser beam, which cause it to emit light in proportion to the amount of energy stored thereon during its exposure to the radiation. The light emitted by the stimulable phosphor sheet, upon stimulation thereof, is photoelectrically detected and converted into an electric image signal. The image signal is then processed and used for the reproduction of the radiation image of the object as a visible image on a recording material.

In order for an image signal to be detected accurately, certain factors which affect the image signal should be set in accordance with the dose of radiation delivered to the stimulable phosphor sheet, and the like. Novel radiation image recording and reproducing systems, which accurately detect an image signal, have been proposed. The proposed radiation image recording and reproducing systems are constituted such that a preliminary read-out operation (hereinafter simply referred to as the "preliminary readout") is carried out in order to approximately ascertain the radiation image stored on the stimulable phosphor sheet. In the preliminary readout, the stimulable phosphor sheet is scanned with a light beam having a comparatively low energy level, and a preliminary read-out image signal obtained during the preliminary readout is analyzed. Thereafter, a final read-out operation (hereinafter simply referred to as the "final readout") is carried out to obtain the image signal, which is to be used for the reproduction of a visible image. In the final readout, the stimulable phosphor sheet is scanned with a light beam having an energy level higher than the energy level of the light beam used in the preliminary readout, and the radiation image is read out with the factors affecting the image signal, which have been adjusted to appropriate values on the basis of the results of an analysis of the preliminary read-out image signal.

In a radiation image read-out apparatus, which is provided with a photodetector for photoelectrically converting the light emitted by the stimulable phosphor sheet, the amplification factor for the analog image signal obtained from photoelectric conversion in the photodetector is controlled such that an image having an appropriate image density can be reproduced. However, the speed, with which the image signal is detected from the stimulable phosphor sheet, has been increased recently. Therefore, the amount of emitted light, which enters the photodetector per unit time, has become large, and the dynamic range of the light emitted by the stimulable phosphor sheet has become wide. Accordingly, in cases where the dose of radiation delivered to the stimulable phosphor sheet is large, it often occurs that an amount of light exceeding the capacity of the photodetector is emitted by the stimulable phosphor sheet. In such cases, the photodetector becomes saturated and cannot generate an image signal corresponding to the dose of radiation delivered to the stimulable phosphor sheet.

It is considered to widen the dynamic range of the photodetector and to improve the performance of the photodetector such that the photodetector can detect a large amount of light emitted by the stimulable phosphor sheet. However, if the dynamic range of the photodetector is widened, it will become difficult to detect a small change in contrast of a reproduced image.

Also, it is considered to adjust the amount of the stimulating rays irradiated to the stimulable phosphor sheet. However, if the amount of the stimulating rays irradiated to the stimulable phosphor sheet is adjusted, the sharpness of an image reproduced from the obtained image signal changes in accordance with the amount of the stimulating rays, and an image having stable sharpness cannot be obtained.

SUMMARY OF THE INVENTION

The primary object of the present invention is to provide a radiation image read-out apparatus, wherein the amount of light emitted by a stimulable phosphor sheet, which light enters a photodetector, is adjusted such that the sharpness of a reproduced image may not change.

Another object of the present invention is to provide a radiation image read-out apparatus, wherein the dynamic range of a photodetector need not be widened, and therefore a small change in contrast of a reproduced image is capable of being detected accurately.

The present invention provides a first radiation image read-out apparatus, wherein a stimulable phosphor sheet, on which a radiation image has been stored, is exposed to stimulating rays, which cause the stimulable phosphor sheet to emit light in proportion to the amount of energy stored thereon during its exposure to radiation, and the emitted light is detected and photoelectrically converted by a photodetector, an image signal representing the radiation image being thereby generated by the photodetector, the radiation image read-out apparatus comprising:

i) a stored energy amount input means, with which the information corresponding to the amount of energy stored on the stimulable phosphor sheet during its exposure to radiation is inputted, and ii) a light amount adjusting means, which is located in an optical path of the emitted light impinging upon the photodetector, and which adjusts the amount of the emitted light impinging upon the photodetector, the adjustment being carried out in accordance with the amount of energy stored on the stimulable phosphor sheet, which energy amount is represented by the information having been inputted with the stored energy amount input means.

The term "information corresponding to the amount of energy stored on a stimulable phosphor sheet during its exposure to radiation" as used herein means, for example, the information concerning the amount of instantaneously emitted light, which is emitted instantaneously by the stimulable phosphor sheet when it is exposed to the radiation, the information concerning an image signal obtained when a preliminary readout is carried out, the information concerning the dose of radiation delivered to an object, or the information concerning a menu which represents the relationship between, for example, the portion of an object the image of which is recorded and the dose of radiation delivered.

The present invention also provides a second radiation image read-out apparatus, wherein the first radiation image read-out apparatus in accordance with the present invention is modified such that the light amount adjusting means may comprise a material, which is located in the optical path of the emitted light impinging upon the photodetector, and the light transmittance of which changes in accordance with the level of voltage applied to it, and a voltage applying means for applying a voltage, which is of a level in accordance with the amount of energy stored on the stimulable phospho sheet, to the material.

As the material, the light transmittance of which changes in accordance with the level of voltage applied to it, it is possible to employ, for example, an electrochromic material, such as a W03 thin film formed on a glass plate provided with ITO transparent electrodes.

The present invention further provides a third radiation image read-out apparatus, wherein the first radiation image read-out apparatus in accordance with the present invention is modified such that the light amount adjusting means may comprise a material, which is located in the optical path of the emitted light impinging upon the photodetector, and the light transmittance of which changes in accordance with the amount of light irradiated to it, and a light irradiating means for irradiating light, which is in an amount in accordance with the amount of energy stored on the stimulable phosphor sheet, to the material.

As the material, the light transmittance of which changes in accordance with the amount of light irradiated to it, it is possible to employ a photochromic material, such as spiropyrane, fulgide, or diarylethene.

The present invention still further provides a fourth radiation image read-out apparatus, wherein the first radiation image read-out apparatus in accordance with the present invention is modified such that the light amount adjusting means may comprise a filter means, which is capable of being inserted into and removed from the optical path of the emitted light impinging upon the photodetector, and which reduces the light transmittance in accordance with the amount of energy stored on the stimulable phosphor sheet, and a filter drive means, which inserts the filter means into the optical path of the emitted light impinging upon the photodetector and removes the filter means from the optical path.

With the radiation image read-out apparatus in accordance with the present invention, the amount of the light emitted by the stimulable phosphor sheet, which light impinges upon the photodetector, is adjusted by the light amount adjusting means in accordance with the information corresponding to the amount of energy stored on the stimulable phosphor sheet, such as the information concerning the amount of instantaneously emitted light or the information concerning the image signal obtained from the preliminary readout, which information has been inputted with the stored energy amount input means. Specifically, in cases where the value of the information having been inputted with the stored energy amount input means is larger than a predetermined information value, the amount of the emitted light impinging upon the photodetector is reduced by the light amount adjusting means. Therefore, even if the amount of the light emitted by the stimulable phosphor sheet is as large as a value going beyond the detection capacity of the photodetector, such a large amount of the emitted light will not impinge upon the photodetector, and only an amount of the emitted light smaller than the detection capacity of the photodetector will impinge upon the photodetector. Accordingly, an image signal corresponding to the dose of radiation delivered to the stimulable phosphor sheet can be generated by the photodetector.

Also, with the radiation image read-out apparatus in accordance with the present invention, the amount of the emitted light impinging upon the photodetector can be adjusted such that the amount of the stimulating rays irradiated to the stimulable phosphor sheet may not be changed. Therefore, the problems can be prevented from occurring in that the sharpness of an image reproduced from the obtained image signal changes in accordance with the amount of the stimulating rays. Further, the dynamic range of the photodetector for detecting the light emitted by the stimulable phosphor sheet need not be widened, and therefore a small change in contrast of a reproduced image can be detected accurately.

The light amount adjusting means may comprise the material, the light transmittance of which changes in accordance with the level of voltage applied to it, and the voltage applying means for applying a voltage, which is of a level in accordance with the amount of energy stored on the stimulable phosphor sheet, to the material. Alternatively, the light amount adjusting means may comprise the material, the light transmittance of which changes in accordance with the amount of light irradiated to it, and the light irradiating means for irradiating light, which is in an amount in accordance with the amount of energy stored on the stimulable phosphor sheet, to the material. As another alternative, the light amount adjusting means may comprise the filter means, which reduces the light transmittance in accordance with the amount of energy stored on the stimulable phosphor sheet, and the filter drive means, which inserts the filter means into the optical path of the emitted light impinging upon the photodetector and removes the filter means from the optical path.

DESCRIPTION OF THE PREFERRED EMBODIMENTS

The present invention will hereinbelow be described in further detail with reference to the accompanying drawings.

Figure 1:
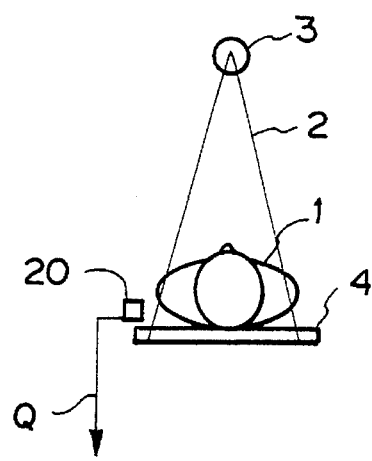
FIG. 1 is a schematic view showing how a radiation image is stored on a stimulable phosphor sheet.

FIG. 1 shows how a stimulable phosphor sheet 4 is exposed to radiation 2, which carries image information of an object 1. As illustrated in FIG. 1, the stimulable phosphor sheet 4 is located at the position for image recording, and a radiation source is activated to produce the radiation 2. The radiation 2 passed through the object 1. The radiation 2, which has passed through the object 1, impinges upon the stimulable phosphor sheet 4, and a radiation image of the object 1 is thereby stored on the stimulable phosphor sheet 4. When the stimulable phosphor sheet 4 is exposed to the radiation 2, which has passed through the object 1, the stimulable phosphor sheet 4 instantaneously emits light. The amount of the instantaneously emitted light is detected by a detection means 20, and detected information Q is generated by the detection means 20.

Figure 2:
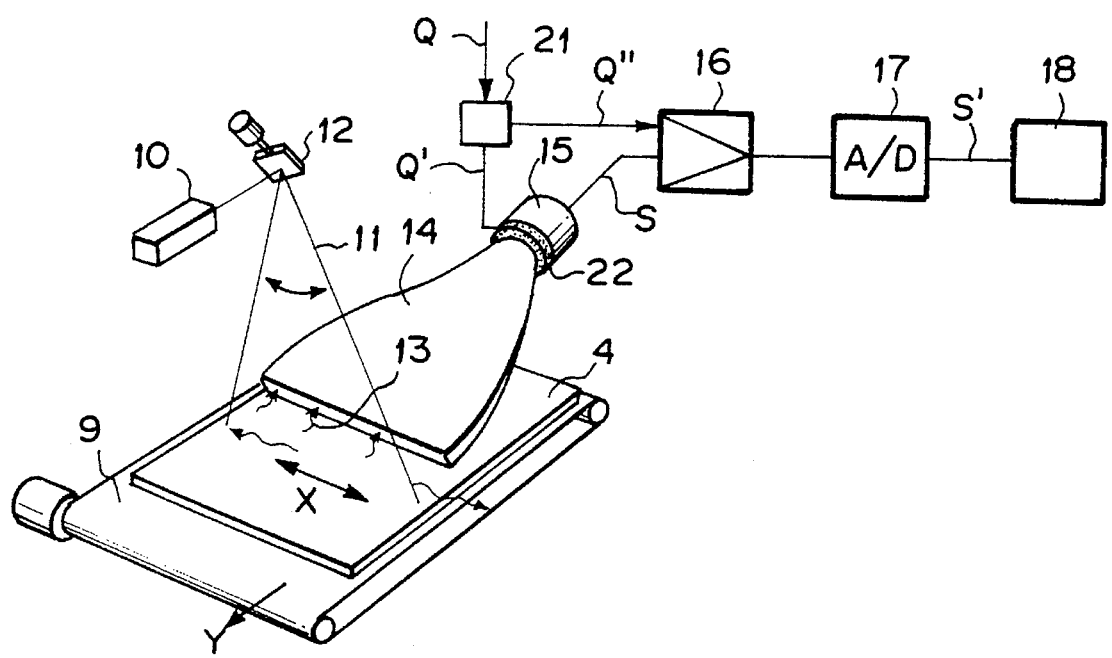
FIG. 2 is a perspective view showing an embodiment of the radiation image read-out apparatus in accordance with the present invention.

How an image signal representing the radiation image is detected from the stimulable phosphor sheet 4 will be described hereinbelow. FIG. 2 is a perspective view showing an embodiment of the radiation image readout apparatus in accordance with the present invention. With the radiation image read-out apparatus shown in FIG. 2, the radiation image stored on the stimulable phosphor sheet 4 is read out, and an image signal representing the radiation image is thereby obtained. How the radiation image read-out apparatus operates will be described hereinbelow.

Figure 3:
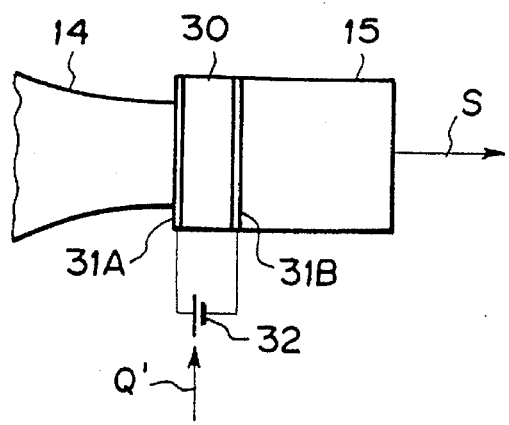
FIG. 3 is a schematic view showing a means for electrically adjusting the amount of emitted light impinging upon a photomultiplier.

The stimulable phosphor sheet 4 is moved by a sub-scanning means 9 in the sub-scanning direction indicated by the arrow Y. The sub-scanning means 9 may be constituted of an endless belt, or the like. A laser beam 11 serving as stimulating rays is produced by a laser beam source 10. While the stimulable phosphor sheet 4 is being moved in the sub-scanning direction, the laser beam 11 is deflected by a scanning mirror 12 and caused to scan the stimulable phosphor sheet 4 in the main scanning directions indicated by the double headed arrow X. When the stimulable phosphor sheet 4 is thus exposed to the stimulating rays, the exposed portion of the stimulable phosphor sheet 4 emits light 13 in proportion to the amount of energy stored thereon during its exposure to radiation. The emitted light 13 enters into a light guide member 14 from its one end face. The light guide member 14 is made by forming a transparent acrylic plate. The emitted light 13, which has entered into the light guide member 14, is guided through repeated total reflection inside of the light guide member 14 and received by a photomultiplier 15. As illustrated in FIG. 3, an electrochromic material 30 is located such that it may be in close contact with a light input end face of the photomultiplier 15 upon which the emitted light 13 impinges. The electrochromic material 30 comprises a $WO_3$ thin film formed on a glass plate provided with ITO transparent electrodes 31A and 31B. An electric power source 32 is connected to the transparent electrodes 31A and 31B. The electric power source 32 is also connected to a control means 21, which is shown in FIG. 2 and which receives the detected information Q from the detection means 20. The control means 21 generates a control signal Q' in accordance with the received detected information Q and thereby controls the voltage, which is applied to the electrochromic material 30. Specifically, in cases where the amount of light, which is instantaneously emitted by the stimulable phosphor sheet 4 when the stimulable phosphor sheet 4 is exposed to the radiation, is larger than a predetermined value, the problems occur in that the amount of the emitted light 13 becomes larger than the detection capacity of the photomultiplier 15, and an image signal cannot be generated accurately. Therefore, in order for such problems to be eliminated, the voltage, which is applied to the electrochromic material 30, is controlled in accordance with the detected information Q, and the light transmittance of the electrochromic material 30 is thereby changed. In this manner, the amount of the emitted light 13 impinging upon the photomultiplier 15 is controlled. Therefore, a large amount of the emitted light 13 going beyond the detection capacity of the photomultiplier 15 does not impinge upon the photomultiplier 15. Accordingly, it is not necessary for the dynamic range of the photomultiplier 15 to be widened, and the image signal corresponding to the dose of radiation delivered to the stimulable phosphor sheet 4 can be generated accurately. In this manner, an image signal S, which corresponds to the amount of the emitted light 13, i.e. which represents the radiation image stored on the stimulable phosphor sheet 4, is generated by the photomultiplier 15.

The image signal S is logarithmically amplified by a logarithmic amplifier 16. An amplification signal Q" is fed from the control means 21 to the logarithmic amplifier 16. In this manner, the image signal S having been obtained by photoelectrically converting the emitted light 13, which has been transmitted with a reduced light transmittance through the electrochromic material 30 to the photomultiplier 15, is amplified by the logarithmic amplifier 16 such that the amplified image signal may correspond to the amount of the light 13 emitted by the stimulable phosphor sheet 4. Therefore, the image signal S can be converted into an image signal, which corresponds to the dose of radiation delivered to the stimulable phosphor sheet 4. The amplified image-signal is fed into an analog-to-digital converter 17 and is thereby converted into a digital image signal S'. The image signal S' is fed into an image reproducing means 18, which may be a cathode ray tube (CRT) display device, or the like. The image reproducing means 18 reproduces the radiation image of the object 1 as a visible image.

In the embodiment described above, the electrochromic material 30 is employed as the means for electrically changing the light transmittance. However, no limitation is imposed on the kind of the means for electrically changing the light transmittance. For example, a liquid crystal may be utilized for this purpose.

Figure 4:
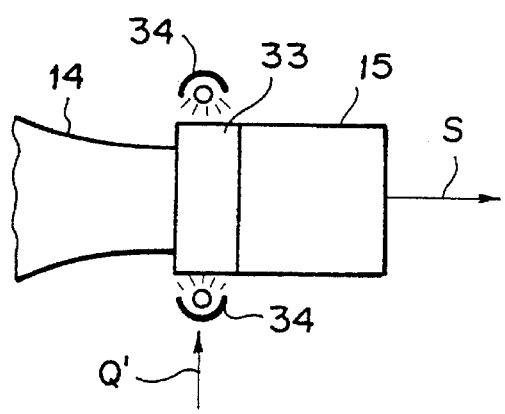
FIG. 4 is a schematic view showing a means for optically adjusting the amount of emitted light impinging upon a photomultiplier.

In the embodiment described above, the electrochromic material 30, the light transmittance of which is changed electrically, is employed as the means for adjusting the amount of the emitted light 13 impinging upon the photomultiplier 15. Alternatively, as illustrated in FIG. 4, a photochromic material 33, the light transmittance of which is changed optically, may be employed as the means for adjusting the amount of the emitted light 13 impinging upon the photomultiplier 15. Specifically, as illustrated in FIG. 4, the photochromic material 33, such as spiropyrane, fulgide, or diarylethene, is located such that it may be in close contact with the light input end face of the photomultiplier 15 upon which the emitted light 13 impinges. Also, ultraviolet light sources 34, 34 are located around the photochromic material 33 and are connected to the control means 21. The control means 21 generates the control signal Q' in accordance with the received detected information Q and thereby controls the amount of light produced by the ultraviolet light sources 34, 34. The photochromic material 33 has the properties such that its light transmittance changes in accordance with the intensity of the light irradiated thereto. As described above, in cases where the amount of light, which is instantaneously emitted by the stimulable phosphor sheet 4 when the stimulable phosphor sheet 4 is exposed to the radiation, is larger than a predetermined value, the problems occur in that the amount of the emitted light 13 becomes larger than the detection capacity of the photomultiplier 15, and an image signal cannot be generated accurately. Therefore, in order for such problems to be eliminated, the amount of light, which is produced by the ultraviolet light sources 34, 34, is controlled in accordance with the detected information Q, and the light transmittance of the photochromic material 33 is thereby changed. In this manner, the amount of the emitted light 13 impinging upon the photomultiplier 15 is controlled.

Figure 5:
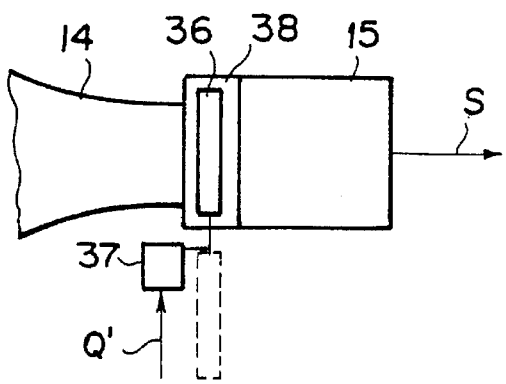
FIG. 5 is a schematic view showing a means for mechanically adjusting the amount of emitted light impinging upon a photomultiplier.

As described above, the amount of the emitted light 13 impinging upon the photomultiplier 15 may be controlled electrically or optically. As another alternative, the amount of the emitted light 13 impinging upon the photomultiplier 15 may be controlled mechanically. For example, as illustrated in FIG. 5, a space 38 may be formed at the light input end face of the photomultiplier 15 upon which the emitted light 13 impinges. A filter means 36, such as an ND filter, is located such that it can be inserted into and removed from the space 38 by a filter drive means 37, which is connected to the control means 21. How the embodiment shown in FIG. 5 operates will be described hereinbelow.

The control means 21 generates the control signal Q' in accordance with the detected information Q received from the detection means 20. The control signal Q' is fed into the filter drive-means 37. The filter drive means 37 inserts the filter means 36 into the space 38 or removes it from the space 38 in accordance with the control signal Q'. Specifically, as described above, in cases where the amount of light, which is instantaneously emitted by the stimulable phosphor sheet 4 when the stimulable phosphor sheet 4 is exposed to the radiation, is larger than a predetermined value, the problems occur in that the amount of the emitted-light 13 becomes larger than the detection capacity of the photomultiplier 15, and an image signal cannot be generated accurately. Therefore, in order for such problems to be eliminated, the filter means 36 is inserted into or removed from the space 38 in accordance with the detected information Q, and the amount of the emitted light 13 impinging upon the photomultiplier 15 is thereby controlled.

Figure 6:
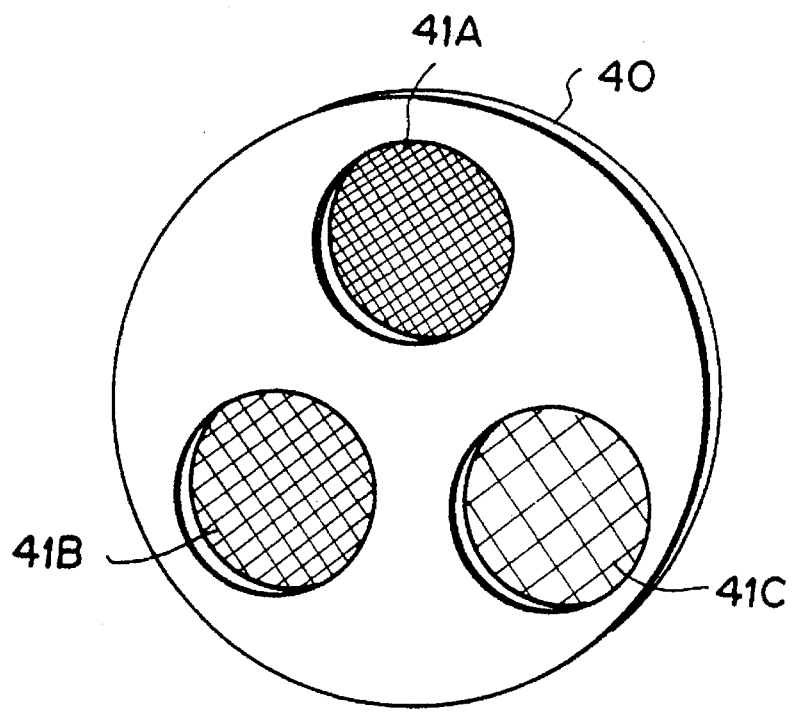
FIG. 6 is a schematic view showing a different example of a filter means.

In the embodiment of FIG. 5, only a single kind of filter is utilized as the filter means 36. Alternatively, a plurality of kinds of filters may be utilized. For example, as illustrated in FIG. 6, three kinds of filters 41A, 41B, and 41C may be located in a disk 40. The disk 40 is rotated in accordance with the control signal Q', and the amount of the emitted light 13 impinging upon the photomultiplier 15 is thereby controlled.

In the embodiments described above, the amount of light, which is instantaneously emitted by the stimulable phosphor sheet 4 when the stimulable phosphor sheet 4 is exposed to the radiation, is detected, and the amount of the emitted light 13 impinging upon the photomultiplier 15 is controlled in accordance with the information thus detected. Alternatively, in cases where the preliminary readout and the final readout are carried out, the amount of the emitted light 13 impinging upon the photomultiplier 15 may be controlled in accordance with the information concerning the image signal obtained from the preliminary readout. As another alternative, the dose of radiation delivered from the radiation source 3 shown in FIG. 1 may be detected directly, and the amount of the emitted light 13 impinging upon the photomultiplier 15 may be controlled in accordance with the results of the detection. As a further alternative, the information concerning a menu, which represents the relationship between, for example, the kind of an object, the portion of an object the image of which is recorded, or the like, and the dose of radiation delivered from the radiation source, may be inputted from an external input means into the control means, and the amount of the emitted light 13 impinging upon the photomultiplier 15 may be controlled in accordance with the inputted menu.

Figure 7:
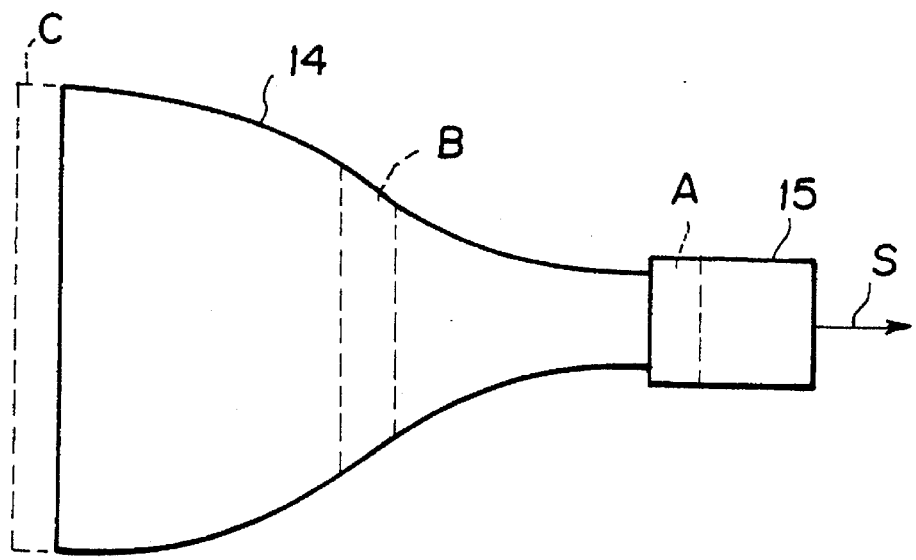
FIG. 7 is an explanatory view showing a position at which a light amount adjusting means is located.

Further, in the embodiments described above, the means for adjusting the amount of the emitted light 13 impinging upon the photomultiplier 15 is located on the light input end face of the photomultiplier 15. However, the means for adjusting the amount of the emitted light 13 impinging upon the photomultiplier 15 may be located at any position in the optical path of the emitted light 13 impinging upon the photomultiplier 15. For example, as illustrated in FIG. 7, the means for adjusting the amount of the emitted light 13 impinging upon the photomultiplier 15 may be located at a light input end face C of the light guide member 14 upon which the emitted light 13 impinges, or at an intermediate point B between the light input end face C and a light output end face of the light guide member 14.

What is claimed is:

1. A radiation image read-out apparatus, wherein a stimulable phosphor sheet, on which a radiation image has been stored, is exposed to stimulating rays, which cause the stimulable phosphor sheet to emit light in proportion to the amount of energy stored thereon during its exposure to radiation, and the emitted light is detected and photoelectrically converted by a photodetector, an image signal representing the radiation image being thereby generated by the photodetector, the radiation image read-out apparatus comprising:

i) a stored energy amount input means, with which the information corresponding to the amount of energy stored on the stimulable phosphor sheet during its exposure to radiation is inputted, and ii) a light amount adjusting means, which is located in an optical path of the emitted light impinging upon the photodetector, and which adjusts the amount of the emitted light impinging upon the photodetector, the adjustment being carried out in accordance with the amount of energy stored on the stimulable phosphor sheet, which energy amount is represented by the information having been inputted with the stored energy amount input means.

2. An apparatus as defined in claim 1 wherein the light amount adjusting means comprises a material, which is located in the optical path of the emitted light impinging upon the photodetector, and the light transmittance of which changes in accordance with the level of voltage applied to it, and a voltage applying means for applying a voltage, which is of a level in accordance with the amount of energy stored on the stimulable phosphor sheet, to said material.

3. An apparatus as defined in claim 1 wherein the light amount adjusting means may comprise a material, which is located in the optical path of the emitted light impinging upon the photodetector, and the light transmittance of which changes in accordance with the amount of light irradiated to it, and a light irradiating means for irradiating light, which is in an amount in accordance with the amount of energy stored on the stimulable phosphor sheet, to said material.

4. An apparatus as defined in claim 1 wherein the light amount adjusting means may comprise a filter means, which is capable of being inserted into and removed from the optical path of the emitted light impinging upon the photodetector, and which reduces the light transmittance in accordance with the amount of energy stored on the stimulable phosphor sheet, and a filter drive means, which inserts the filter means into the optical path of the emitted light impinging upon the photodetector and removes the filter means from the optical path.

5. An apparatus as defined in claim 1 wherein the information corresponding to the amount of energy stored on the stimulable phosphor sheet during its exposure to the radiation is the information concerning the amount of instantaneously emitted light, which is emitted instantaneously by the stimulable phosphor sheet when it is exposed to the radiation.

6. An apparatus as defined in claim 1 wherein the information corresponding to the amount of energy stored on the stimulable phosphor sheet during its exposure to the radiation is the information concerning an image signal obtained when a preliminary readout is carried out on the stimulable phosphor sheet.

7. An apparatus as defined in claim 1 wherein the information corresponding to the amount of energy stored on the stimulable phosphor sheet during its exposure to the radiation is the information concerning the dose of radiation delivered to an object the radiation image of which is recorded on the stimulable phosphor sheet.

8. An apparatus as defined in claim 1 wherein the information corresponding to the amount of energy stored on the stimulable phosphor sheet during its exposure to the radiation is the information concerning a menu representing the relationship between specifics about an object, the radiation image of which is recorded, and the dose of radiation delivered from a radiation source.

9. An apparatus as defined in claim 2 wherein the material, the light transmittance of which changes in accordance with the level of voltage applied to it, is an electrochromic material.

10. An apparatus as defined in claim 3 wherein the material, the light transmittance of which changes in accordance with the amount of light irradiated to it, is a photochromic material.

11. An apparatus as defined in claim 1 wherein the stimulating rays are a laser beam.

12. An apparatus as defined in claim 1 wherein the stimulable phosphor sheet is two-dimensionally scanned with the stimulating rays.

* * * * *